(12) United States Patent
Mayo

(10) Patent No.: US 6,224,374 B1
(45) Date of Patent: May 1, 2001

(54) FIXED, SPLINTED AND REMOVABLE PROSTHESIS ATTACHMENT

(76) Inventor: Louis J. Mayo, 1340 Hill Crest Rd., Cincinnati, OH (US) 45224-3226

( * ) Notice: Subject to any disclaimer, the term of this patent is extended or adjusted under 35 U.S.C. 154(b) by 0 days.

(21) Appl. No.: 09/598,816

(22) Filed: Jun. 21, 2000

(51) Int. Cl.[7] .................................................. A61C 13/12
(52) U.S. Cl. ............................................. 433/180; 433/181
(58) Field of Search .................................... 433/180, 181, 433/182, 183

(56) References Cited

U.S. PATENT DOCUMENTS

| | | |
|---|---|---|
| 2,826,814 * | 3/1958 | Sappey et al. .................... 433/180 X |
| 4,457,714 * | 7/1984 | Klein .................................... 433/180 |
| 4,758,162 | 7/1988 | Dobbs . |
| 4,775,320 * | 10/1988 | Marshall et al. ................. 433/180 X |
| 4,950,162 * | 8/1990 | Korber et al. ....................... 433/180 |

* cited by examiner

*Primary Examiner*—Nicholas D. Lucchesi
(74) *Attorney, Agent, or Firm*—Wood, Herron & Evans, LLP

(57) ABSTRACT

A dental device for use as a fixed bridge, splint or removable prosthesis attachment. The device includes a bench framework adapted to be bonded to an internal axial surface of a tooth cavity preparation. The device may include one or more pontics for securing between adjacent natural teeth. The device may further include two members having mating wells for holding magnets to provide a removable prosthesis.

32 Claims, 4 Drawing Sheets

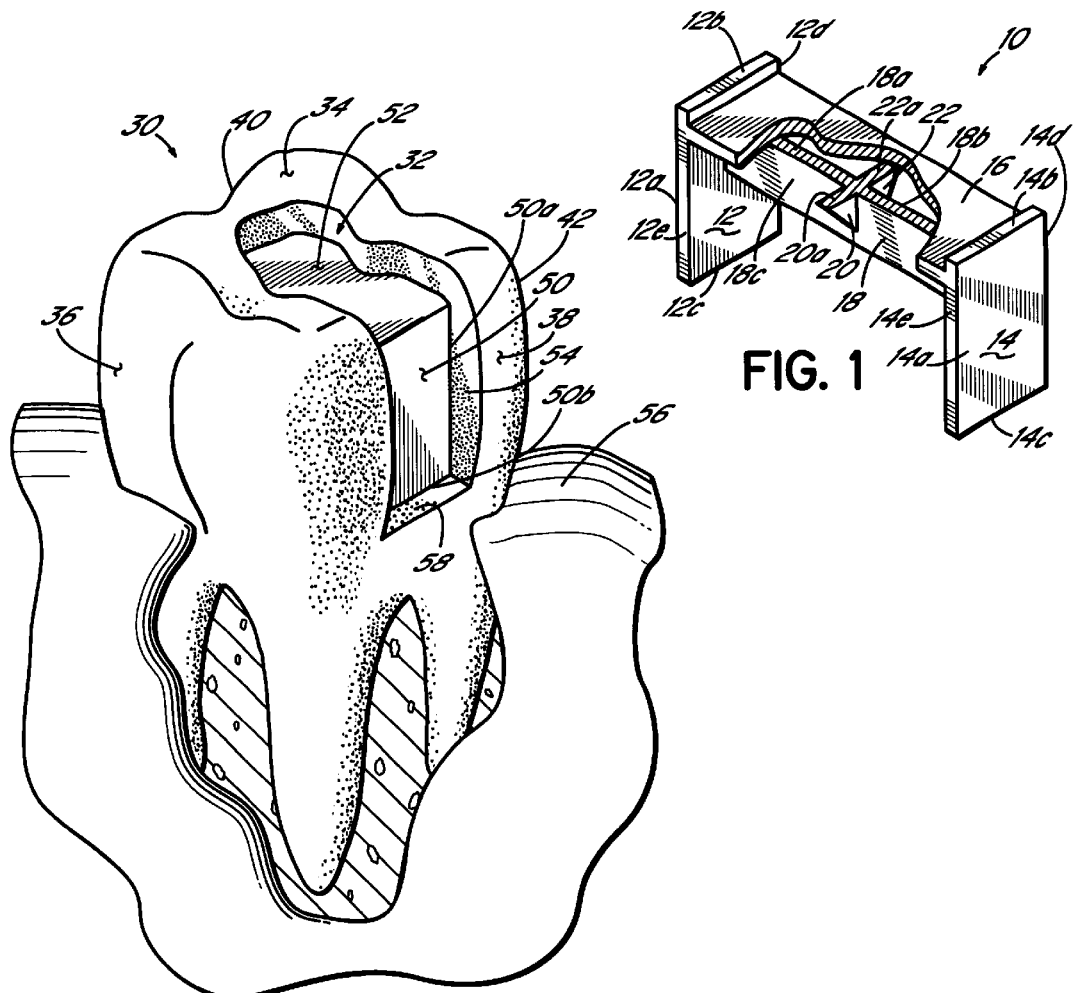
FIG. 1
FIG. 2
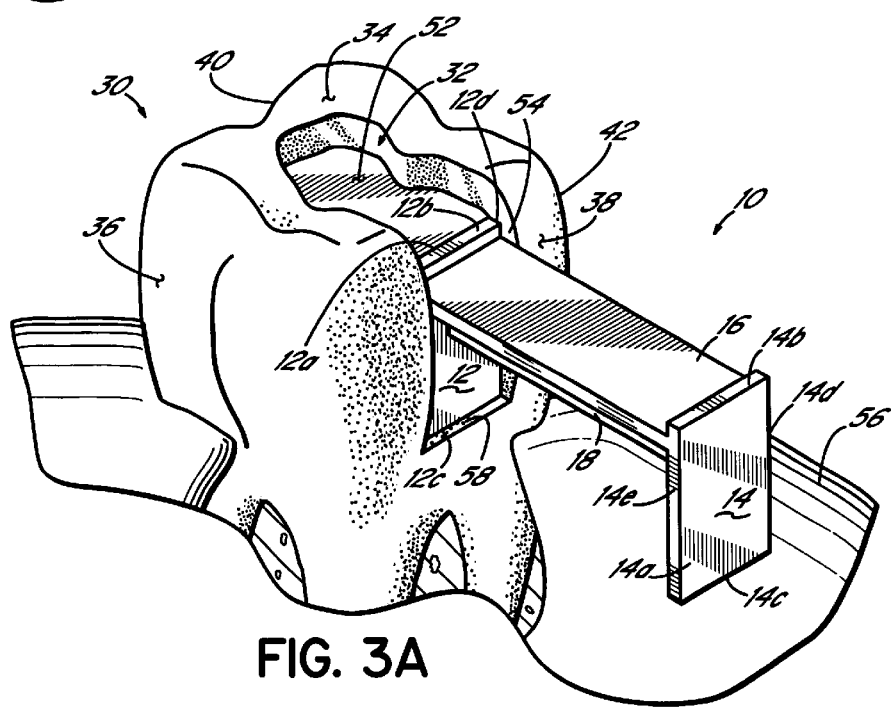
FIG. 3A

FIXED, SPLINTED AND REMOVABLE PROSTHESIS ATTACHMENT

FIELD OF THE INVENTION

This invention relates to dental tooth replacement and splinting devices.

BACKGROUND OF THE INVENTION

Fixed bridge prosthetic replacements for missing teeth and splinted prostheses are generally well known in the art of dentistry and in widespread use. In a typical fixed bridge, one or more abutment supporting teeth located on either side of the span of missing teeth are used to suspend a row of false teeth, referred to as pontics, in a manner that cements or bonds the false teeth to the enamel of naturally occurring teeth so that the wearer cannot remove the structure (i.e., it is fixed in place). A fixed bridge design having abutment-supporting teeth on only one side of the span of missing teeth is referred to as a cantilever fixed bridge. A fixed splint connects two or more adjacent teeth to provide a brace for weakly supporting members of the combined structure and is used to reduce or prevent mobility of weakly supported teeth. A fixed splint does not necessarily contain pontic replacements of missing teeth but is cemented or bonded in a manner similar to fixed bridges.

Previously, conventional fixed bridges were accomplished by the attachment of crowns, inlays, onlays or a combination of these structures with suitable cement to the prepared (or shaped) abutment-supporting teeth. The shaped abutment-supporting teeth were then reproduced in form and position for a waxed facsimile to be cast by means of the lost wax process with the completed fixed bridge containing the abutment restorations, pontics, and any veneer or covering for increased aesthetics. The pontic replacements are attached to the abutment restorations via unit casting or by soldering. This process, from start to finish, requires a high degree of dental and technical custom fabrication skill, many patient appointments, removal of significant portions of tooth structure that may be otherwise sound, accurate impression technique and materials, a temporary fixed bridge to keep the shaped abutment-supporting teeth in a stable position, and is costly. Consequently, much of the progress in fixed bridge construction has focused upon reducing many of these disadvantages of the conventional fixed bridge while, at the same time, reducing the cost.

With increased use of bonded resins and new technology in etched metal fabrication, bonded resin metal-based fixed bridges became possible. These structures, referred to collectively as Maryland-type bridges, bond metal connectors externally to the enamel of abutment-supporting teeth. The fixed placement of the bridge, however, is totally dependent upon the bonding vehicle. The metal connectors must cover a significant width and more than half the circumference of the abutment tooth enamel in addition to an occlusal rest seat for adequate bonding to prevent displacement. The large amount of visible metal makes this type of bridge non-aesthetic and frankly unsightly. Moreover, the bonding technique is highly sensitive to moisture, which results in a weakened bond. The structure is susceptible to forces causing torque and, therefore, is contraindicated in cantilever fixed bridge designs and where some of the abutment-supporting teeth are mobile. Bonding strength to the external surfaces of the enamel is seriously jeopardized by inherently weak and poorly mineralized enamel. Failure of the structure to remain fixed is a direct result of the failure of the bond to the external surfaces of the enamel. The Maryland-type bridge, moreover, is a custom fabrication process accomplished in a dental prosthetics laboratory.

More recently, a fixed bridge composed almost exclusively of bonded resin is proposed under the trade name "California Bridge", of Kulzer Laboratory, Inc. of Irvine, Calif. The resin fixed bridge abrades down more easily against natural dentition and against porcelain-covered opposing teeth than do porcelain restorations. Moreover, it requires that the teeth be prepared for the restoration, an impression made of the prepared sites, and temporary fillings placed between patient appointments. A thin nondescript metal substructure may be used solely to support the pontic. The resin fixed bridge is inherently weak, particularly over longer pontic spans. In principle, this bridge is no different than a conventional fixed bridge except that the dental material used for the California fixed bridge design is made of resin compatible with current bonding techniques.

Fixed splints that make use of castings, model construction or indirect fabrication restorations utilize techniques and materials similar to fixed bridges. The splint restoration is cast as one piece or soldered into a single unit having no pontic and cemented to adjacent natural teeth to lock them together.

More direct in-mouth techniques exist to rigidly hold teeth that are otherwise loose or mobile. All of the direct techniques are variations of materials for the purpose of splinting teeth. Stainless steel wire may be used to wrap around the exteriors of both loose teeth and the more stable teeth to which they are splinted; the wire may then be covered or attached with acrylic or resin. This technique of ligation is commonly practiced. Other materials are used for splints without the need to wrap the affected teeth. A mesh of stainless steel, titanium, silk or other material adapted to the lingual surfaces of anterior teeth and covered with resin has been used. Notched or perforated metal bars of either stainless steel or other suitable metal alloys have been used for the purpose of splinting teeth. In this technique, long grooves are cut across the occlusal surfaces of adjacent teeth, the bar placed at the base of the groove preparation, and the groove filled with resin to lock mobile teeth to more stable adjacent teeth. One such splinting bar resembling a miniature I-beam, referred to as "Titanium Splinting Bar", commercially available from Zeza (Davie, Fla.), is used for immediate space maintenance, splinting for periodontally loose teeth and repair of broken solder joints of prosthetic appliances.

The replacement of missing teeth may also be accomplished with the use of a removable prosthesis, sometimes referred to as a "partial denture". The removable partial denture is indicated where the arrangement and/or the supporting strength of the remaining teeth in the oral cavity cannot support a fixed bridge. Removable partial dentures are comparatively less expensive than fixed prostheses and can be used when cost to the patient is an overriding factor. The position of the removable partial prosthesis is stabilized in the oral cavity by a system of connectors to the abutment natural teeth.

The connectors clamp externally around the abutment-supporting teeth and are called clasps. This type of clamping mechanism around natural teeth is both unpleasant in its appearance and a significant accumulator of bacterial plaque, causing tooth decay against the surfaces of the teeth needed to support the stability of the removable partial denture.

Connectors are also fabricated with interlocking members so that one member is cast into a newly constructed crown with the corresponding member attached to the partial denture. The designs of the interlocking members are numerous but each requires that a crown be fabricated which is costly, requires high dental proficiency, removes unnecessary tooth structure and is time consuming. Additionally, the interlocking components of the partial and the crown wear against one another rapidly and are not readily repairable except with fabrication of a new appliance.

There is thus a need to develop fixed bridges, splints and removable prosthesis attachments having a simplified construction that eliminates the need for customized bridge construction, simplifies dental chairside procedures, reduces destruction of sound tooth structure and generally lowers cost.

SUMMARY OF THE INVENTION

The present invention provides a dental device for use as a fixed bridge, splint or removable prosthesis attachment. The device, which is supported by resin-based filling materials, has a framework resistant to the vertical forces of occlusion and torque generated by mastication. The devices of the present invention derive high bond strength from the large internal surface area of a proximal box of a prepared tooth by taking advantage of the axial wall, the gingival floor and the internal-facing walls of the cavity preparation. The bench framework of the device of the present invention provides the structural support for the bonding resin within the box as well as the functional support for the proposed uses of the device.

To this end, and in accordance with the principles of the present invention, a dental device is provided having substantially simplified construction including lateral support members for bonding to the axial wall and gingival floor of proximal box preparations in adjacent teeth, and a primary support member for connecting the lateral support members, and when needed to support one or more pontics. In an alternative embodiment of the present invention, a single lateral support member is provided for bonding within a proximal box preparation of a natural tooth, the member including a magnet within a retention well, and a removable prosthetic member having a retention cap with a magnet therein for placement over the retention well, the magnets being attracted to each other to retain the retention cap in removable relation to the prepared tooth. In the alternative, the single lateral support member within the proximal box may be attached to other types of connectors for the purpose of providing attachment between abutment teeth and a removable prosthesis. There are thus provided fixed bridges, splints and removable prosthesis attachments that eliminate many aspects of customized bridge construction, simplify dental chairside procedures, reduce the reduction of sound tooth structure and lower the cost of prosthesis construction. These and other objects and advantages of the present invention shall become more apparent from the accompanying drawings and description thereof

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the principles of the invention.

FIG. 1 is a perspective view, partially cut away, of a dental bench structural support device constructed in accordance with the principles of the present invention;

FIG. 2 is a perspective view of a tooth having a proximal box preparation adapted to receive the device of FIG. 1;

FIG. 3A depicts in perspective view the device of FIG. 1 placed in an upright position in the proximal box of FIG. 2 for fixed bridge prosthesis construction;

DETAILED DESCRIPTION

Figure 3B:
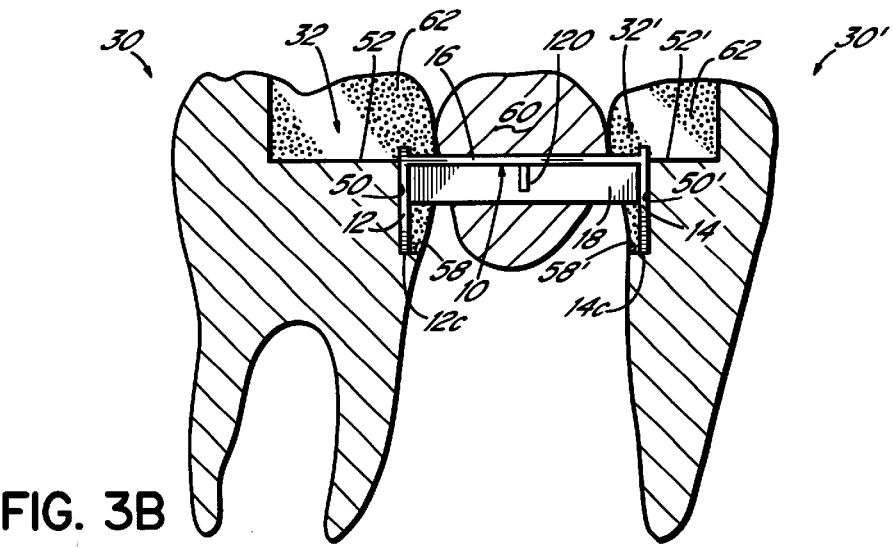
FIG. 3B depicts in cross-sectional view taken longitudinally generally along the line of the dental arch a device of the present invention having a pontic affixed thereto, and bonded in an upright position in proximal boxes of adjacent teeth.

The present invention provides a dental device that may be used as a fixed bridge, splint or removable prosthesis attachment, wherein the device has a bench framework that may be manufactured rather than custom fabricated and which provides stress transfer in such a way to promote distributed concentrations of stress to supporting abutment teeth. The device of the present invention requires routine dental skills in common dental practice rather than highly specialized skill, retains cosmetic appearance, and minimizes cost through reduced patient chair time.

Referring to the drawings, FIG. 1 depicts an exemplary embodiment of the present invention. The dental device 10 is a bench framework including a pair of lateral support members 12,14 connected by a primary support member 16. The lateral support members 12,14 have outer planar surfaces 12a,14a for attaching to adjacent teeth, as will be discussed in more detail below. The primary support member 16 is preferably horizontal and perpendicular to the lateral support members 12,14, but may be angled as appropriate for a particular patient. The dental device 10 may further include a secondary support member 18 attached on a top edge surface 18a to the primary support member 16 and attached on its end edge surfaces (not shown) to respective lateral support members 12,14. This secondary support member 18 provides a bracing support for the primary support member 16 and provides increased rigidity to inhibit vertical deflection of the primary support member 16, even under the stress of mastication. Additional support may also be provided by a pair of supplemental support members 20,22, also called third support members, which connect the primary 16 and secondary 18 support members. Advantageously, top edge surfaces 20*a*,22*a* of the third support members 20,22 are affixed to the primary support member 16 and respectively affixed to sides 18*b*,18*c* of the secondary support member 18. These supplemental support members 20,22 may provide additional support particularly where the primary support member 16 is of significant length, width or height relative to the lateral support member as well as provide additional retention for the pontic.

Referring now to FIG. 2, there is shown the anatomy of a prepared tooth 30, in this illustration a lower right molar, with the essential parts of a proximal box preparation 32. The tooth 30 has five surfaces exposed in the oral cavity: the occlusal surface 34 that faces the chewing surfaces of the opposing dental arch (not shown); the buccal surface 36 that faces the cheek in the posterior region of the mouth (or the facial or labial surface that faces the lips in the anterior region of the mouth); the mesial surface 38 that faces forward along the dental arch; the distal surface 40 that faces toward the rear of the dental arch; and the lingual surface 42 that faces the tongue for a tooth in the mandible (or palatal surface for a tooth in the maxilla). In this illustration, the proximal box preparation 32 is formed in the mesial surface 38 and occlusal surface 34 of the tooth 30. The term "proximal" refers to a tooth surface that faces the next tooth in line of the same dental arch, which would generally be the mesial surface 38 or distal surface 40 of the tooth 30. It is to be understood, that while the proximal box preparation 32 is depicted on the mesial surface 38 of a lower right molar, the present invention is applicable to any tooth in the mouth.

In the lower right molar depicted in FIG. 2, the proximal box preparation 32 includes an exposed axial wall 50 in the mesial surface 38 of the tooth 30 essentially parallel to the long axis of the tooth 30, and an exposed pulpal floor 52 in the occlusal surface 34 of the tooth 30. From the side edges 50*a* of the axial wall 50 outwardly toward the mesial surface 38 of the tooth 30 are the facing walls 54 of the cavity preparation 32. From the bottom edge 50*b* of the axial wall 50 closest to the gum line 56 extending outwardly to the mesial surface 38 of the tooth 30 is the gingival floor 58 of the proximal box 32.

In use, as shown in FIG. 3A, the outer surface 12*a* of a lateral support member 12 of the device 10 of FIG. 1 is placed in abutting relation to the axial wall 50 of the proximal box preparation 32 with a bottom edge surface 12*c* resting upon the gingival floor 58 of the proximal box 32 and opposing side edge surfaces 12*d*,12*e* abutting the facing walls 54 of the proximal box 32. The axial wall 50 and lateral support member 12 are parallel to the long axis of the tooth 30, thus taking advantage of a large internal bonding surface. The lateral support member 12 may be affixed within the proximal box 32 by any suitable means such as conventional dental cementing or bonding resin. For example, these resins include composite resin systems well known to those in the dental field.

Figure 3C:
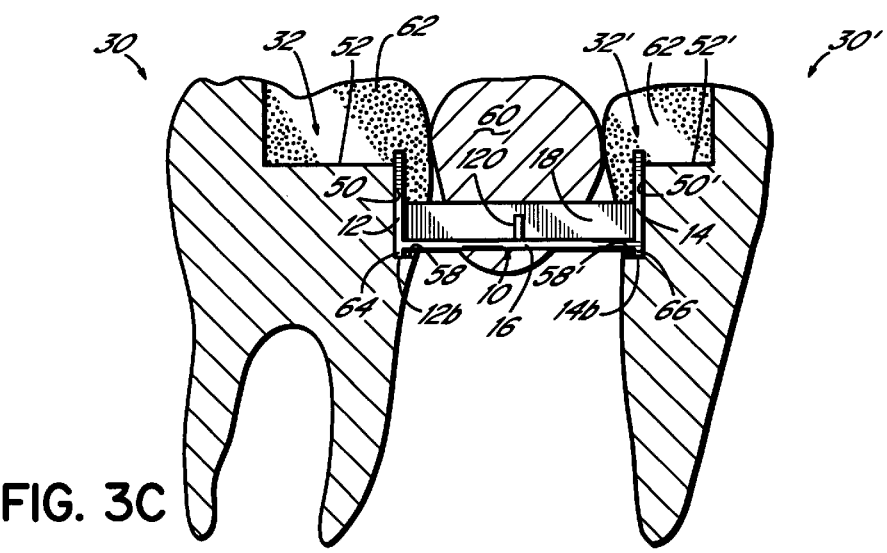
FIG. 3C depicts in cross-sectional view taken longitudinally generally along the line of the dental arch a device of the present invention having a pontic affixed thereto, and bonded in an inverted position within proximal boxes of adjacent teeth.
Figure 3D:
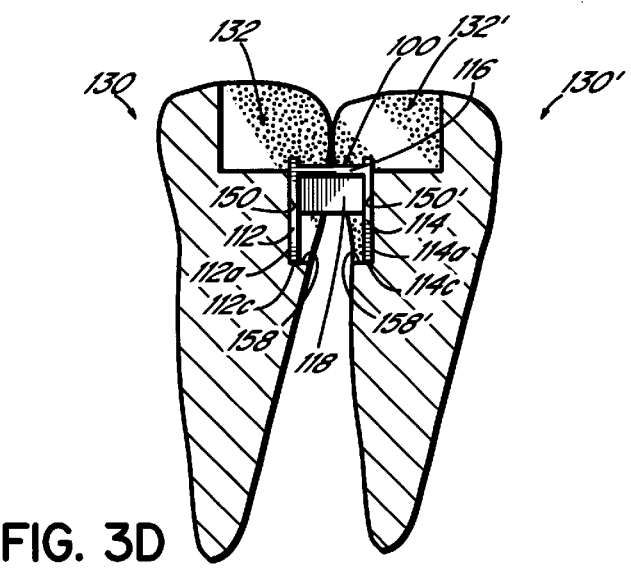
FIG. 3D depicts in cross-sectional view taken longitudinally generally along the line of the dental arch a device of the present invention in a minimized configuration to splint the position of two adjoining teeth.

The present invention is further depicted in FIGS. 3B–3D. In FIG. 3B, the dental device includes a pontic 60 attached to the primary 16 and secondary 18 support members between the lateral support members 12,14. The lateral support members 12,14 are affixed to the axial walls 50,50' of two adjacent teeth 30,30'. The primary support member 16 connects the lateral support members 12,14 remote from the edge surfaces 12*c*,14*c* in contact with the gingival floors 58,58'. Bonded resin 62 is added into the proximal boxes 32,32' on the pulpal floors 52,52' and surrounding the dental device 10 to secure the device 10 and pontic 60 between the adjacent teeth 30,30'. In FIG. 3C, the dental device 10 is inserted in an inverted position with the primary support member 16 connecting the lateral support members 12,14 proximate to the edge surfaces 12*b*,14*b* contacting the gingival floors 58,58'. Preferably, in this embodiment, the lateral support members include heel portions 64,66 extending between the primary support member 16 and the edge surfaces 12*b*,14*b* contacting the gingival floors 58,58'. Again, the dental device 10 may include a pontic 60 affixed to the primary 16 and secondary 18 support members. The pontic 60 may be affixed by any known or future developed method, such as molding the pontic 60 around the support members, and/or mechanically fastening the pontic to the device 10. In FIG. 3D, a splinting device 100 is depicted connecting to adjacent teeth 130,130' without an intermediate pontic. The splinting device 100 is simply a minimized configuration of device 10 of sufficient length to secure two abutting teeth 130,130' together, whereas the device 10 of FIGS. 3B and 3C are of sufficient length to support a pontic 60 between the abutting teeth 30,30'. Thus, device 100 includes a pair of lateral support members 112,114 connected by a primary support member 116. Outer planar surfaces 112*a*,114*a* are attached to the axial walls 150,150' of teeth 130,130' with edge surfaces 112*c*,114*c* resting on the gingival floors 158,158' of proximal boxes 132,132'. Device 100 may further include a secondary support member 118.

In each embodiment of FIGS. 3B–3D, it is shown that the device of the present invention is attached to an internal axial surface of the tooth parallel, or substantially parallel, to the long axis of the tooth. Moreover, this axial wall has a large surface area for attachment. These aspects, in combination with the bench design, provide a device that has high bond strength and structural integrity and maintains its function under the forces produced by mastication.

Figure 4A:
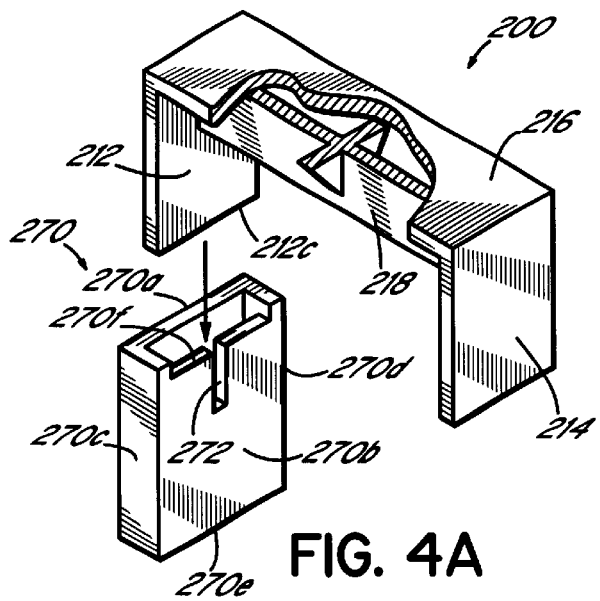
FIG. 4A depicts in perspective view an alternative embodiment of the present invention including a sleeve member.
Figure 4B:
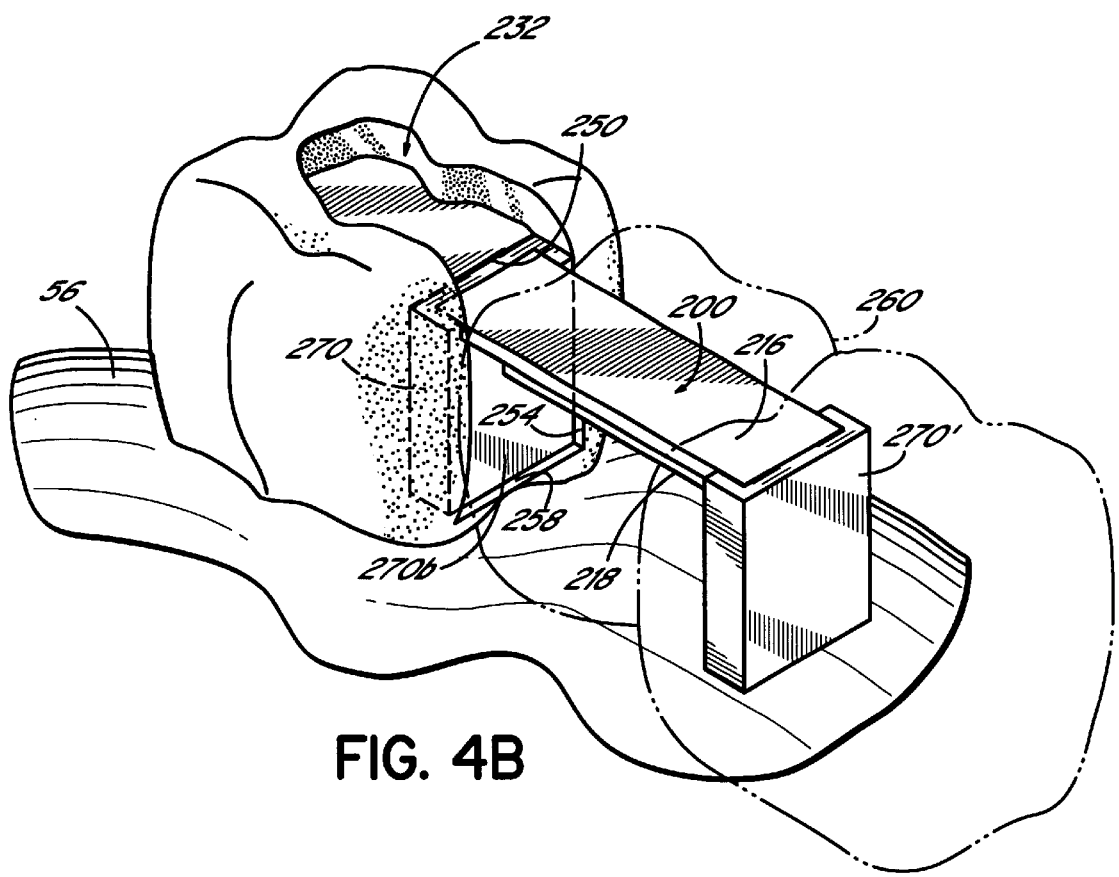
FIG. 4B depicts in perspective view placement of the sleeve of FIG. 4A inside the proximal box of a tooth and insertion of a device of the present invention into the sleeve.

Another exemplary embodiment of the present invention is depicted in FIGS. 4A–4C. As shown in FIG. 4A, the dental device 200 further includes a sleeve member 270 for receiving a lateral support member 212. The outer surface 270*a* of the sleeve member 270 is then affixed to the axial wall 250 of the proximal box preparation 232 as depicted in FIGS. 4B and 4C. The side surfaces 270*c*,270*d* likewise abut the facing walls 254 of proximal box 232 and the bottom surface 270*e* rests on the gingival floor 258. Advantageously, the inner surface 270*b* of the sleeve member 270 is shorter than the outer surface 270*a* such that the primary support member 216 oriented remote from the bottom edge surface 212*c* of lateral support member 212 rests upon a top edge 270*f* of the inner surface 270*b* of the sleeve member 270. Where the dental device 200 includes a secondary support member 218, the sleeve member 270 further includes a slot 272 adapted to receive that secondary support member 218. As shown in FIGS. 4B and 4C, a sleeve member 270,270' is provided for each of the lateral support members 212,214 of the dental device 200 of FIG. 4A. In FIG. 4B, a single pontic 260 is affixed to the primary support member 216 between the lateral support members 212,214. Not illustrated, more than one pontic 260 may be affixed to the primary support member 216 when the primary support member 216 is of a length to provide sufficient room for more than one pontic 260.

Figure 5A:
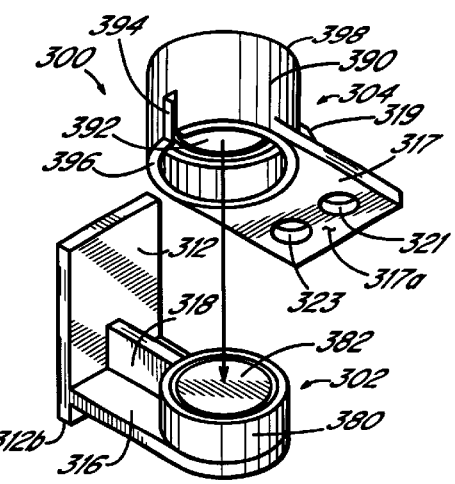
FIG. 5A depicts in perspective view an alternative embodiment of a device of the present invention including a retention well attachment for removable partial prosthesis construction.
Figure 5B:
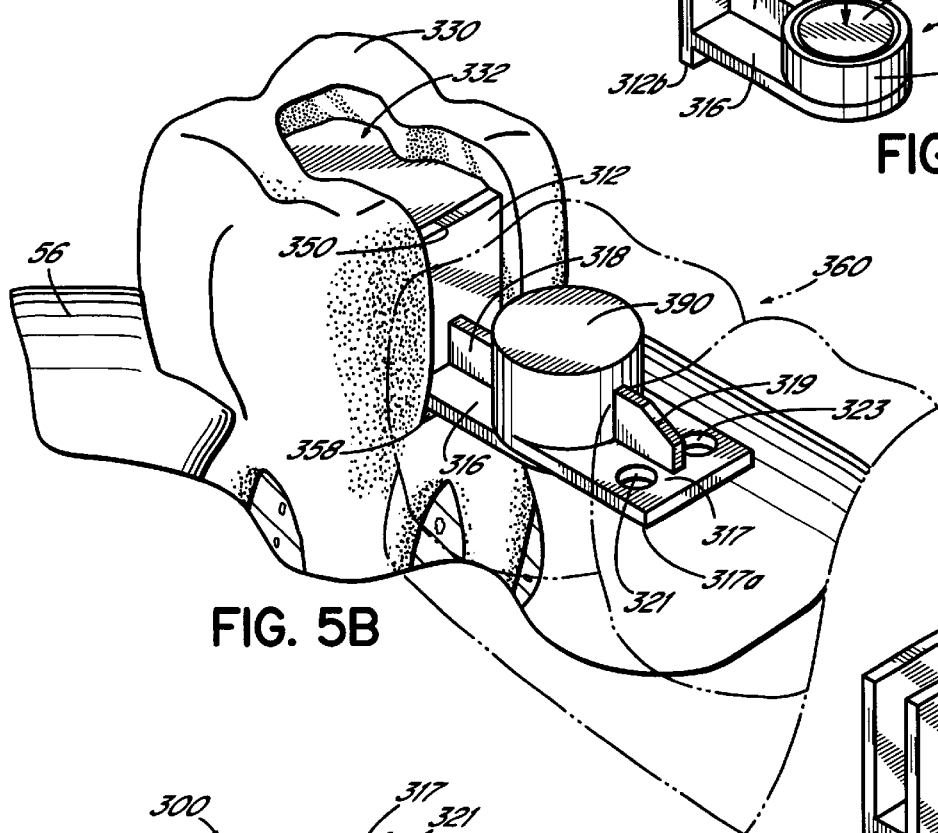
FIG. 5B depicts in perspective view placement of the device of FIG. 5A in a proximal box of a tooth.
Figure 5C:
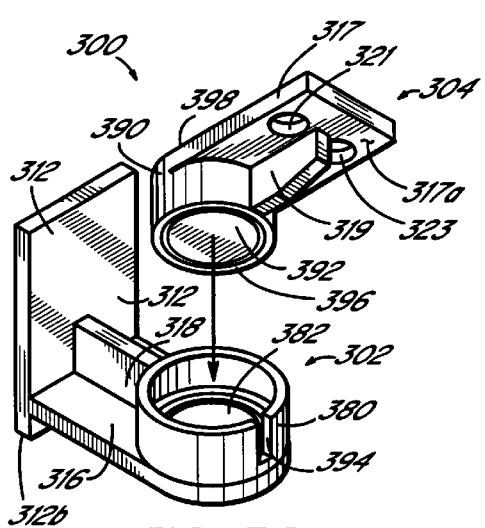
FIG. 5C depicts in perspective view an alternative embodiment of the device of FIG. 5A.

Yet another exemplary embodiment of the present invention is depicted in FIGS. 5A and 5B. A dental device 300 includes a first member 302 having a lateral support member 312 for affixing to the axial wall 350 of a proximal box preparation 332. Attached to the lateral support member 312 proximate to the edge surface 312b for contacting the gingival wall 358 is a primary support member 316. Attached to the opposite end of that primary support member 316 is a retention well 380. Within the retention well 380 is housed a magnet 382. A second member 304 is provided having a primary support member 317 and a retention cap 390 at one end adapted to cover the retention well 380. The retention cap 390 is also provided with a magnet 392 therein configured to attract to the magnet 382 in the retention well 380. Opposite the retention cap 390, the primary support member 317 is affixed to a removable prosthesis of teeth 360. In this regard, retention holes 321,323 may be provided in primary support member 317 to receive material and thereby prevent second member 304 from sliding out of the removable prosthesis of teeth 360. Where the primary support member 316 of the first member 302 includes a secondary support member 318, the retention cap 390 includes a slot 394 for receiving the secondary support member 318. Primary support member 317 may also include a secondary support member 319. A portion of the row of prosthetic teeth 360 is formed over the retention cap 390. In use, the magnets 382,392 hold the removable row of prosthetic teeth 360 in place adjacent to natural tooth 330, and upon lifting upwardly on the removable row of prosthetic teeth 360, the magnets 382,392 will release to allow removal of the second member 304, leaving the first member 302 still attached within the proximal box 332 of tooth 330. Additional prosthetic teeth may be added to removable prosthesis 360 by extending primary support member 317 of the second member 304. Primary support member 317 is preferably oriented proximate the open end 396 of retention cap 390. Alternatively, as depicted in FIG. 5C, retention cap 390 may be sized so as to fit within retention well 380 by placing the primary support member 317 toward the top 398 of the retention cap 390 and forming a slot 394 in the retention well 380 to receive a secondary support member 319 attached on the underside 317a of primary support member 317.

Figure 6A:
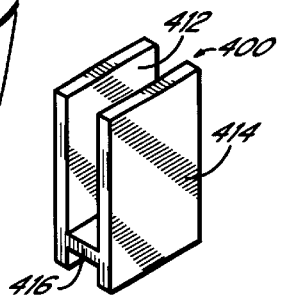
FIG. 6A depicts in perspective view a splint support for connecting one posterior tooth to an adjacent posterior tooth.
Figure 6B:
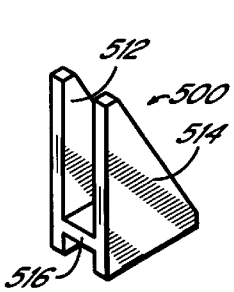
FIG. 6B depicts in perspective view a splint support for connecting an anterior tooth to an adjacent anterior tooth.
Figure 6C:
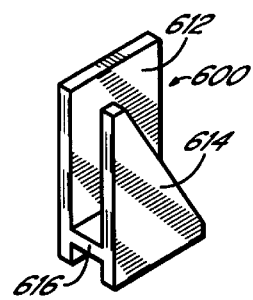
FIG. 6C depicts in perspective view a splint support for connecting a posterior tooth to an adjacent anterior tooth.

Lastly, exemplary embodiments are provided for splint devices 400,500,600 of the present invention as depicted in FIGS. 6A–6C. FIG. 6A depicts a splinting device 400 for splinting two adjacent posterior teeth (not shown). The device 400 includes two rectangular lateral support member 412,414 connected by a primary support member 416. The lateral support members 412,414 are adapted to be affixed to axial walls of proximal box preparations in adjoining posterior teeth. FIG. 6B depicts a device 500 for splinting adjacent anterior teeth (not shown). The device 500 includes substantially triangular-shaped lateral support members 512, 514 connected by primary support member 516. Due to the shape and size of anterior teeth, which have a more narrow dimension occlusally than posterior teeth, the proximal box preparation will include an axial wall that is smaller than that of a posterior tooth and having a more triangular shape. Thus, the lateral support members 512,514 of device 500 are adapted to be affixed to the axial walls of proximal box preparations in adjacent anterior teeth. FIG. 6C depicts a device 600 for splinting a posterior tooth to an adjacent anterior tooth. The device 600 includes a substantially rectangular lateral support member 612 and a substantially triangular lateral support member 614 connected by a primary support member 616. Lateral support member 612 is adapted to affixed within the proximal box preparation of a posterior tooth. Lateral support member 614 is adapted to be affixed to the axial wall of a proximal box preparation of an anterior tooth.

The devices of the present invention may be fabricated from precious or nonprecious metals or alloys thereof, or may be pre-formed from plastic, wax or any other material suitable for subsequent casting of the device with the prosthetic structure, where the material permits ease of modification and/or casting. The devices may be made of varying lengths, widths and heights to accommodate any given application.

While the present invention has been illustrated by the description of an embodiment thereof, and while the embodiment has been described in considerable detail, it is not intended to restrict or in any way limit the scope of the appended claims to such detail. Additional advantages and modifications will readily appear to those skilled in the art. The invention in its broader aspects is therefore not limited to the specific details, representative apparatus and method and illustrative examples shown and described. Accordingly, departures may be made from such details without departing from the scope or spirit of applicant's general inventive concept.

What is claimed is:

1. A dental device for use as a fixed bridge, splint or removable prosthesis in a space between adjacent abutment-supporting teeth, comprising:

first and second lateral support members each having a surface adapted to be affixed to an axial wall within a respective proximal box preparation in one of the abutment-supporting teeth and a contact edge surface adapted to be affixed to a gingival floor surface within the respective proximal box preparation; and a substantially rectangular primary support member connecting the first and second lateral support members and configured to traverse the space between the adjacent abutment-supporting teeth, the primary support member having a larger surface adapted to be affixed substantially parallel to the gingival surfaces.

2. The dental device of claim 1 wherein the first lateral support member is substantially rectangularly shaped to be affixed within the proximal box preparation in a posterior tooth and the second lateral support member is substantially rectangularly shaped to be affixed within the proximal box preparation in an adjacent posterior tooth to form a splint between the two posterior teeth.

3. The dental device of claim 1 wherein the first lateral support member is substantially rectangularly shaped to be affixed within the proximal box preparation in a posterior tooth and the second lateral support member is substantially triangularly shaped to be affixed within the proximal box preparation in an adjacent anterior tooth to form a splint between the posterior tooth and anterior tooth.

4. The dental device of claim 1 wherein the first lateral support member is substantially triangularly shaped to be affixed within the proximal box preparation in an anterior tooth and the second lateral support member is substantially triangularly shaped to be affixed within the proximal box preparation in an adjacent anterior tooth to form a splint between the two anterior teeth.

5. The dental device of claim 1 wherein the primary support member is affixed to at least one pontic, wherein the at least one pontic is adapted to seat in the space between the pair of adjacent abutment-supporting teeth when the first and second lateral support members are affixed within the respective proximal box preparations.

6. The dental device of claim 1 further comprising a secondary support member attached on a top edge surface to the primary support member and attached on opposite end edge surfaces to the respective first and second lateral support members.

7. The dental device of claim 6 further comprising a pair of third support members affixed to the primary support member adjacent the top edge surface of the secondary support member and to respective sides of the secondary support member.

8. The dental device of claim 1 wherein the primary support member connects the first and second lateral support members proximate to the contact edge surface.

9. The dental device of claim 8 wherein the first and second lateral support members include a heel portion extending between the primary support member and the contact edge surface.

10. The dental device of claim 1 wherein the primary support member connects the first and second lateral support members remote from the contact edge surface.

11. The dental device of claim 10 further including a pair of sleeve members adapted to be affixed to the axial wall and gingival floor surface of the respective proximal box preparation, each sleeve member including a cavity configured to receive the respective first and second lateral support member.

12. The dental device of claim 11 further comprising a secondary support member attached on a top edge surface to the primary support member and attached on opposite end edge surfaces to the respective first and second lateral support members, wherein the sleeve members each further include a slot configured to receive the secondary support member.

13. A dental device for use as a fixed bridge, splint or removable prosthesis in a space between adjacent abutment-supporting teeth, comprising:
first and second lateral support members each having a surface adapted to be affixed to an axial wall within a respective proximal box preparation in one of the abutment-supporting teeth and an edge surface adapted to be affixed to a gingival floor surface within the respective proximal box preparation;
a primary support member connecting the first and second lateral support members and configured to traverse the space between the adjacent abutment-supporting teeth;
a secondary support member attached on a top edge surface to the primary support member and attached on opposite end edge surfaces to the respective first and second lateral support members; and
at least one pontic affixed to the primary support member, wherein the at least one pontic is adapted to seat in the space between the pair of adjacent abutment-supporting teeth when the first and second lateral support members are affixed within the respective proximal box preparations.

14. The dental device of claim 13 further comprising a pair of third support members affixed to the primary support member adjacent the top edge surface of the secondary support member and to respective sides of the secondary support member.

15. The dental device of claim 13 wherein the primary support member connects the first and second lateral support members proximate to the contact edge surface.

16. The dental device of claim 13 wherein the first and second lateral support members include a heel portion extending between the primary support member and the contact edge surface.

17. The dental device of claim 13 wherein the primary support member connects the first and second lateral support members remote from the contact edge surface.

18. The dental device of claim 13 further including a pair of sleeve members adapted to be affixed to the axial wall and gingival floor surface of the respective proximal box preparation, each sleeve member including a cavity configured to receive the respective first and second lateral support member and a slot configured to receive the secondary support member.

19. A dental device for use as a removable prosthesis, comprising:
a first member including:
(a) a lateral support member having a surface adapted to be affixed to an axial wall within a proximal box preparation in a natural tooth and a contact edge surface adapted to be affixed to a gingival floor surface within the proximal box preparation; and
(b) a first primary support member having a first end attached to the lateral support member, and having a second end attached to a retention well, the well containing a first magnet; and
a second member including:
(a) a second primary support member having a first end attached to a prosthetic tooth and a second end attached to a retention cap, the cap containing a second magnet configured to attract to the first magnet in the well; and
(b) a pontic affixed to the retention cap, wherein the retention cap of the second member is configured to receive the retention well of the first member in releasable engagement to provide a removable prosthesis.

20. The dental device of claim 19 further comprising a first secondary support member attached on a bottom edge surface to the first primary support member, attached on a first end edge surface to the lateral support member, and attached on a second end edge surface to the retention well.

21. The dental device of claim 19 further comprising a second secondary support member attached on a bottom edge surface to the second primary support member and attached on an end edge surface to the retention cap.

22. The dental device of claim 19 wherein the retention cap is configured to cover the retention well.

23. The dental device of claim 19 wherein the retention cap is configured to fit within the retention well.

24. A dental device for use as a fixed bridge, splint or removable prosthesis in a space between adjacent abutment-supporting teeth, comprising:
first and second lateral support members each having a surface adapted to be affixed to an axial wall within a respective proximal box preparation in one of the abutment-supporting teeth and a contact edge surface adapted to be affixed to a gingival floor surface within the respective proximal box preparation;
a primary support member connecting the first and second lateral support members remote from the contact edge surface and configured to traverse the space between the adjacent abutment-supporting teeth;
a secondary support member attached on a top edge surface to the primary support member and attached on opposite end edge surfaces to the respective first and second lateral support members; and
a pair of sleeve members adapted to be affixed to the axial wall and gingival floor surface of the respective proximal box preparation, each sleeve member including a cavity configured to receive the respective first and second lateral support member and a slot configured to receive the secondary support member.

25. The dental device of claim 24 further comprising at least one pontic affixed to the primary support member, wherein the at least one pontic is adapted to seat in the space between the pair of adjacent abutment-supporting teeth when the first and second lateral support members are affixed within the respective proximal box preparations.

26. A dental device for use as a fixed bridge, splint or removable prosthesis in a space between adjacent abutment-supporting teeth, comprising:

first and second lateral support members each having a surface adapted to be affixed to an axial wall within a respective proximal box preparation in one of the abutment-supporting teeth and a contact edge surface adapted to be affixed to a gingival floor surface within the respective proximal box preparation;

a primary support member connecting the first and second lateral support members and configured to traverse the space between the adjacent abutment-supporting teeth; and a secondary support member attached on a top edge surface to the primary support member and attached on opposite end edge surfaces to the respective first and second lateral support members.

27. The dental device of claim 26 wherein the first lateral support member is substantially rectangularly shaped to be affixed within the proximal box preparation in a posterior tooth and the second lateral support member is substantially rectangularly shaped to be affixed within the proximal box preparation in an adjacent posterior tooth to form a splint between the two posterior teeth.

28. The dental device of claim 26 wherein the first lateral support member is substantially rectangularly shaped to be affixed within the proximal box preparation in a posterior tooth and the second lateral support member is substantially triangularly shaped to be affixed within the proximal box preparation in an adjacent anterior tooth to form a splint between the posterior tooth and anterior tooth.

29. The dental device of claim 26 wherein the first lateral support member is substantially triangularly shaped to be affixed within the proximal box preparation in an anterior tooth and the second lateral support member is substantially triangularly shaped to be affixed within the proximal box preparation in an adjacent anterior tooth to form a splint between the two anterior teeth.

30. The dental device of claim 26 further comprising a pair of third support members affixed to the primary support member adjacent the top edge surface of the secondary support member and to respective sides of the secondary support member.

31. The dental device of claim 26 wherein the primary support member connects the first and second lateral support members proximate to the contact edge surface.

32. The dental device of claim 31 wherein the first and second lateral support members include a heel portion extending between the primary support member and the contact edge surface.

* * * * *